United States Patent
Giorgino et al.

(10) Patent No.: US 10,413,596 B2
(45) Date of Patent: Sep. 17, 2019

(54) PHARMACOLOGICAL USE OF A MYOKINE ABLE TO PRESERVE THE FUNCTION AND MASS OF THE PANCREATIC CELLS UNDER DYSMETABOLIC CONDITIONS

(71) Applicant: UNIVERSITA' DEGLI STUDI DI BARI, Bari BA (IT)

(72) Inventors: Francesco Giorgino, Bari BA (IT); Annalisa Natalicchio, Bari BA (IT); Nicola Marrano, Bari BA (IT)

(73) Assignee: UNIVERSITA' DEGLI STUDI DI BARI, Bari (IT)

( * ) Notice: Subject to any disclaimer, the term of this patent is extended or adjusted under 35 U.S.C. 154(b) by 0 days.

(21) Appl. No.: 15/773,762

(22) PCT Filed: Jul. 21, 2016

(86) PCT No.: PCT/IB2016/054339
§ 371 (c)(1),
(2) Date: May 4, 2018

(87) PCT Pub. No.: WO2017/081556
PCT Pub. Date: May 18, 2017

(65) Prior Publication Data
US 2018/0326015 A1    Nov. 15, 2018

(30) Foreign Application Priority Data

Nov. 10, 2015   (IT) ............................... UB2015A5439

(51) Int. Cl.
*A61K 38/00*   (2006.01)
*A61K 38/39*   (2006.01)
*A61P 1/18*    (2006.01)

(52) U.S. Cl.
CPC .............. *A61K 38/39* (2013.01); *A61P 1/18* (2018.01)

(58) Field of Classification Search
None
See application file for complete search history.

(56) References Cited

FOREIGN PATENT DOCUMENTS

CN    104623640 A    *    5/2015
CN    104725500 A    *    6/2015

OTHER PUBLICATIONS

International search report and written opinion dated Nov. 2, 2016 for PCT/IB2016/054339.
International Preliminary Report on Patentability dated May 15, 2018 for PCT/IB2016/054339.
Database WPI Thomson Scientific, London, GB XP002758306 & CN 104 623 640 A Univ Nanjing Medical May 20, 2015.
Database WPI Thomson Scientific, London, GB XP002758307 & CN 104 725 500 A Guangzhou Jiankun Biological Technology Jun. 24, 2015.
Database WPI Thomson Scientific, London, GB XP002758308 & KR 2015 0025480 A Univ Kyungpook Nat Hospital Mar. 10, 2015.
Jian-Jun Liu et al "Lower circulating irisin is associated ith type 2 diabetes melitus" Journal of Diabetes and its complications, vol. 27 No. 4, Jul. 1, 2013.
Natalicchio et al. Exendin-4 Prevents c-Jun N-Terminal Protein Kinase Activation by Tumor Necrosis Factor-$\alpha$ (TNF$\alpha$) and Inhibits TNF$\alpha$-Induced Apoptosis in Insulin-Secreting Cells Article in Endocrinology 151(5):2019-29—Mar. 2010.
McCluskey JT et al—J Biol Chem. Jun. 24, 2011;286(25):21982-92. doi: 10.1074/jbc.M111.226795. Epub Apr. 22, 2011. Development and functional characterization of insulin-releasing human pancreatic beta cell lines produced by electrofusion.
Li et al "A protocol for islet isolation from mouse pancreas" Article (PDF Available) in Nature Protocol 4(11):1649-52—Oct. 2009 DOI: 10.1038/nprot.2009.150—Source: PubMed.
Masini et al "Autophagy in human type 2 diabetes pancreatic beta cells". Diabetologia. Jun. 2009;52(6):1083-6. doi: 10.1007/s00125-009-1347-2. Epub Apr. 15, 2009.

* cited by examiner

*Primary Examiner* — Jeanette M Lieb
(74) *Attorney, Agent, or Firm* — Silvia Salvadori

(57) ABSTRACT

Object of the present invention is the use of a known protein, irisin, for preservation of the functionality and survival of the cells of the pancreatic islets.

8 Claims, 6 Drawing Sheets

Specification includes a Sequence Listing.

a b a b c a b a b

PHARMACOLOGICAL USE OF A MYOKINE ABLE TO PRESERVE THE FUNCTION AND MASS OF THE PANCREATIC CELLS UNDER DYSMETABOLIC CONDITIONS

RELATED APPLICATIONS

This application is the US national phase application of international application number PCT/IB2016/054339, filed 21 Jul. 2016, which designates the US and claims priority to Italian application UB2015A005439 filed 10 Nov. 2015, the contents of each of which are hereby incorporated by reference as if set forth in their entireties.

ABSTRACT OF THE INVENTION

Object of the present invention is the use of a known protein, irisin, for the preservation of the functionality and survival of the cells of the pancreatic islets.

TECHNICAL FIELD AND STATE OF THE ART

Diabetes mellitus is a chronic disease characterized by the presence of high blood glucose levels (hyperglycemia) and caused by an abnormal amount and/or activity of insulin. Insulin is a hormone, produced by pancreas, which allows glucose to enter the cells and later is used as energy source. If there are alterations in the amount or mechanisms of action of insulin, glucose is accumulated in the circulatory system.

Several types of diabetes mellitus are known; the most known and common are: type 1 diabetes mellitus, type 2 diabetes mellitus and gestational diabetes mellitus.

Type 2 diabetes mellitus (DM2) constitutes about 80-90% of all diabetes cases. Two fundamental alterations contribute to the pathogenesis of DM2: on the one hand, an insulin resistance state (i.e., a reduced sensitivity of peripheral tissues to the insulin action), and on the other hand an inadequate secretion of insulin by pancreatic beta-cells. The latter represent, under normal conditions, 50-80% of the endocrine cells found in the pancreatic islets, or Langerhans islets, and guarantee continuous and fast adjustment of the insulin secretion during the variation of the metabolic demand of the organism. A fundamental mechanism causing the DM2 is represented by a dysfunction of the beta-cells and/or a reduction of their number which is responsible for the reduced production and secretion of insulin and for an alteration of the secretion dynamics. It is important to highlight that glycemia does not reach pathological values and DM2 does not occur if, even in presence of insulin resistance, the functionality of the pancreatic beta-cells is maintained intact. For example, the chronic exposure of beta-cells to high levels of free fatty acids, as it occurs in obese subjects, represents one of the main causes of dysfunction and death of the beta-cells, thus generating a predisposition condition to DM2.

The actual DM2 therapy provides for a change in the lifestyle (diet and physical activity) and comprises the use of insulin-sensitizing drugs (biguanides, glitazones) and secretagogues drugs (sulfonylureas, incretins).

Metformin, belonging to the family of biguanides, is one of the most used drugs for the treatment of type 2 diabetes mellitus. Its main effect is to reduce the amount of glucose released by the liver in the bloodstream. However, metformin has not clear protective effects on the pancreatic beta-cells and possesses side-effects such as nausea, vomit and diarrhea.

Glitazones, often used in combination with metformin or sulfonylureas, may cause weight gain and water retention.

Sulfonylureas stimulate the continuous insulin production by the pancreas, thus leading to high risk of hypoglycemia events. Moreover, sulfonylureas can cause weight gain, nausea and diarrhea and do not provide protective effects on the survival of pancreatic beta-cells, on the contrary they could damage them as evidenced by some experimental studies and from the fact that sulfonylurea therapy loses its efficiency with time.

Incretins are an efficient aid in the diabetes therapy. They include GLP-1 analogues (exenatide, liraglutide and lixisenatide), which have the disadvantage of being administered subcutaneously, and the DPP-IV inhibitors (Linagliptin, Saxagliptin, Sitagliptin, Vildagliptin, Alogliptin). The different therapies actually available, in addition to involve several side-effects, constitute a relevant cost for the health care expenditure.

OBJECTS OF THE INVENTION

Object of the present invention is to provide a compound that could be used for the preservation of the functionality and/or the number of cells of the Langerhans islets, i.e. of the pancreatic islets.

Another object of the present invention is to provide a compound that allows to increase the synthesis and/or secretion of insulin by the pancreatic beta-cells.

Still another object of the present invention is to provide a compound that could be used alone or in combination with other therapies for the treatment and/or prevention of pathological or dysmetabolic conditions of pancreas.

DESCRIPTION OF THE INVENTION

The above mentioned objects and still other objects that will be better clarified in the following, are achieved by the present invention, whose object is the use of irisin for the preservation of the functionality and survival of the cells of the pancreatic islets.

In fact, it has been surprisingly observed an interaction ("cross-talk") between the skeletal muscle and pancreas. In particular, it has been observed that irisin, a myokine derived from the cleavage of a membrane precursor named fibronectin type III domain-containing protein 5 (FNDC5), and produced in the skeletal muscle mainly as a consequence of physical activity, can carry out protective effect on the survival and proliferation of the cells of the pancreatic islets, particularly under pathological conditions or metabolic stress. It has been also unexpectedly observed that irisin can induce the production and secretion of insulin by pancreatic beta-cells.

Several functions of irisin are known; for example, it is known that irisin can improve metabolic alterations characterizing obesity thanks to the ability of promoting the "browning" of adipose tissue, i.e., a conversion of white adipose tissue to brown adipose tissue, with higher energy expenditure, by means of the activation of the UCP1 mitochondrial protein.

Moreover, it is known that irisin can prevent the heart damage due to ischemia/reperfusion.

Further studies known in the art highlighted that irisin plays beneficial effects on the bone, muscle and endothelial cells. In particular, it has been observed that irisin aids the in vitro osteoblast differentiation, promotes the activation of the muscle metabolism in C2C12 cells by inducing the biogenesis and the mitochondrial uncoupling and stimulates the proliferation of HUVEC endothelial cells by means of the ERK signaling pathway.

Moreover, it is known that irisin induces, at pharmacological doses, the proliferation of H19-7 murine hippocampal neural cells.

Object of the present invention is irisin for the use in the preservation of the functionality and survival of the cells of the pancreatic islets.

With the terms "preservation of the functionality and survival of the cells of the pancreatic islets", "preservation of the cells of the pancreatic islets", or "preservation" it is meant herein the conservation of the proper number of the cells of the pancreatic islets and of their normal functionality, as well as the conservation of optimal levels of synthesis and secretion of insulin by the pancreatic beta-cells.

Preferably the cells of the pancreatic islets, to which the present invention refers, object of such preservation, are beta-cells.

The experimental results, described herein in the following, allowed to observe the ability of irisin to induce the synthesis and to stimulate the secretion of glucose-induced insulin by the pancreatic beta-cells. Moreover, it has been observed that irisin promotes the proliferation of beta-cells and reduces the death induced by the chronic exposure to saturated fatty acids ("lipotoxic" damage). The lipotoxic damage, i.e., the damage to cells caused by the exposure to high levels of fatty acids (in particular of saturated fatty acids), is responsible for the alteration of the insulin secretion and reduction of the number of pancreatic beta-cells. Irisin, according to the present invention, is advantageously used for the preservation of the pancreatic cells, preferably beta-cells, of the pancreatic islets.

Preferably, the preservation of the pancreatic beta-cells by employing irisin, according to the present invention, comprises the ability of inducing the insulin synthesis. In fact, irisin is advantageously used to stimulate the pancreatic beta-cells to increase the insulin synthesis. This aspect of the present invention is particularly advantageous, e.g., in even pathological conditions, wherein the proper production (i.e., the proper synthesis) of insulin is compromised.

For example, according to an aspect of the present invention, irisin is advantageously used to induce the synthesis of insulin in the pancreatic beta-cells.

According to a preferred embodiment of the present invention, the preservation of the pancreatic beta-cells by employing irisin comprises the stimulation of the insulin secretion.

This aspect of the present invention is in particular advantageous, for example, in even pathological conditions, wherein insulin is not secreted by pancreatic beta-cells in sufficient amounts.

For example, according to an aspect of the present invention, irisin can be used to induce the secretion of insulin in the pancreatic beta-cells.

According to a further embodiment, the preservation of the cells of the pancreatic islets by employing irisin, according to the present invention, comprises the promotion of the proliferation of the cells of the pancreatic islets.

This aspect of the invention if particularly advantageous, since irisin can be used to increase the number of the pancreatic cells, i.e. to increase the cellular mass, for example in conditions wherein pancreas underwent a structural damage that caused the destruction of the cells of the Langerhans islets.

For example, irisin can be used to promote the proliferation of the cells of the pancreatic islets, preferably of the beta-cells.

According to a preferred embodiment of the present invention, the preservation of the cells of the pancreatic islets by using irisin comprises the reduction of the death of said cells of the pancreatic islets.

With the term "death" it is meant the apoptosis, an ordered and regulated process of programmed cell death; under normal condition, apoptosis contributes to the maintenance of the proper cell number of a system but, under pathological or dysmetabolic conditions, it can lead to abnormal or detrimental reduction of the cell mass (or population).

As already mentioned, the preservation of the cells of the pancreatic islets by using irisin, according to the present invention, comprises the reduction of the death of said cells of the pancreatic islets.

It has been in fact observed that irisin can preserve the cell mass of the pancreatic islets, e.g. of the beta-cells, by preventing the reduction of their number as it occurs, for example, under pathological conditions and/or in presence of stimuli able to damage the pancreatic cells thus favoring their apoptosis.

Preferably, the preservation of the cells of the pancreatic islets by using irisin comprises the reduction of the apoptosis of said cells of the pancreatic islets.

For example, according to an aspect of the present invention, irisin can be used to prevent the apoptosis of the pancreatic cells, preferably of the beta-cells.

In a preferred embodiment of the present invention, the preservation of the cells of the pancreatic islets comprises the reduction of the death of said cells of the pancreatic islets caused by the exposure of said cells of the pancreatic islets to saturated fatty acids.

This aspect of the invention is particularly advantageous, since the chronic exposure of the beta-cells to high levels of free fatty acids, as it occurs in obese subjects with or without DM2, constitutes one of the major reasons of dysfunction and death of the beta-cells of the Langerhans islets.

In fact, the chronic exposure of the beta-cells to high levels of free fatty acids causes reduction of the cell mass as final effect, i.e. it causes reduction of the cell number, for example by inducing apoptosis of these cells.

It has been now surprisingly observed that irisin is advantageously used to protect the cells of the pancreatic islets, in particular the beta-cells, from the damage caused by the exposure to high levels of fatty acids, in particular of saturated fatty acids, i.e. from the "lipotoxic" damage.

For example, according to another aspect of the present invention, irisin is used to reduce the apoptosis of the cells of the pancreatic islets, preferably of the beta-cells, caused by the exposure of said pancreatic cells to saturated fatty acids.

In a preferred embodiment of the present invention, the preservation of the cells of the pancreatic islets comprises the reduction of the death of said cells of the pancreatic islets caused by the exposure of said cells of the pancreatic islets to one or more cytotoxic stimuli.

According to the present invention, the use of irisin for the preservation of the cells of the pancreatic islets involves the induction of the insulin synthesis in the pancreatic beta-cells and the stimulation of the insulin secretion by said cells. Moreover, still according to the present invention, the use of irisin for the preservation of the cells of the pancreatic islets involves the promotion of the proliferation of the cells of the pancreatic islets and the reduction of the death of the same cells (e.g. the death by apoptosis), preferably when the cell death is caused by a lipotoxic damage.

Still object of the present invention is a composition comprising irisin for the use in the preservation of the functionality and survival of the cells of the pancreatic islets.

Preferably, compositions comprising irisin for the use according to the present invention further comprise excipients and/or additives of pharmaceutical use, e.g. excipients and/or additives known in the art.

The irisin administration can occur, for example, parenterally, preferably subcutaneously.

Irisin is used in doses ranging from 20 to 100 nM. Irisin is administered in vivo in murine models, at doses ranging from 1 to 20 μg a day, by means of peritoneal injection.

The carried out experiments allowed to observe the surprising efficiency of irisin in the preservation of the functionality and survival of the cells of the pancreatic islets, preferably in the preservation of the pancreatic beta-cells.

In particular, it has been observed that the conditioned medium from myocytes exposed to palmitate (i.e. a saturated fatty acid) for 4 h can protect the pancreatic beta-cells from the apoptosis induced by the fatty acid; on the contrary, the exposure to palmitate for 24 h increases the beta-cells death. This observation is coherent with the observation that irisin is produced by rat and human myocytes when exposed to palmitate for 4 h, but not for 24 h.

Moreover, it has been observed that mice fed with High Fat Diet (HFD) showed increased serum irisin levels with respect to mice fed with a standard diet.

It has therefore surprisingly observed that irisin can stimulate the synthesis and secretion of insulin in the pancreatic beta-cells, promote the proliferation of said cells and protect them from the "lipotoxic" damage, i.e. from the damages induced by the prolonged exposure to high concentrations of fatty acids, in particular of saturated fatty acids.

Therefore, according to the present invention, irisin is advantageously used in the preservation (i.e. in the protection and conservation of the proper activity and proper number) of the cells of the Langerhans islets, preferably of the beta-cells of these islets.

The present invention, whose object is the use of irisin for the preservation of the cells of the pancreatic islets, is advantageously applied in the treatment and prevention of diseases caused by, or causing as a consequence thereof, a pancreas damage, in particular the damage or death of the cells of the pancreatic islets. For example, irisin can be used to preserve the cells of the pancreatic islets in the context of the treatment and/or prevention of pancreas diseases or dysmetabolic conditions such as, for example, diabetes mellitus, in particular type 2 diabetes mellitus and, more generally, of all the diseases wherein a pancreas damage occurs.

The following experimental evidences are reported as a further support of the present invention.

The experimental results are associated with the appended Figures.

EXPERIMENTAL SECTION

Experiments have been carried out on L6 rat myoblasts differentiated in myotubes using a low serum concentration (2%) medium and used at the seventh day of differentiation; on human myoblasts isolated from biopsies of the rectus abdominis by tripsine digestion, differentiated in myotubes using a low serum concentration (2%) medium and used at the fifth day of differentiation; on INS-1E rat insulinoma cells cultured as described in the literature (Natalicchio A, De Stefano F, Orlando M R, Melchiorre M, Leonardini A, Cignarelli A, et al. Exendin-4 prevents c-Jun N-terminal protein kinase activation by tumor necrosis factor-alpha (TNFalpha) and inhibits TNFalpha-induced apoptosis in insulin-secreting cells. Endocrinology. 2010 May; 151(5): 2019-29); on 1.1B4 human pancreatic beta-cells (McCluskey J T, Hamid M, Guo-Parke H, McClenaghan N H, Gomis R, Flatt P R. Development and functional characterization of insulin-releasing human pancreatic beta cell lines produced by electrofusion. J Biol Chem. 2011 June; 286(25):21982-92); on murine pancreatic islets isolated by perfusion of the bile duct and digestion in collagenase (Li D-S, Yuan Y-H, Tu H-J, Liang Q-L, Dai L-J. A protocol for islet isolation from mouse pancreas. Nat Protoc. 2009 January; 4(11):1649-52) and used within 3 days from the isolation; on human pancreatic islets isolated as previously described (Masini M, Bugliani M, Lupi R, del Guerra S, Boggi U, Filipponi F, et al. Autophagy in human type 2 diabetes pancreatic beta cells. Diabetologia [Internet]. 2009 June [cited 2014 Nov. 24]; 52(6):1083-6. Available from: http://www.ncbi.nlm.nih.gov/pubmed/19367387).

To carry out the experiments human recombinant irisin produced into *E. coli* has been used, which is compatible with all the used cell systems, due to the 100% amino acid sequence identity among the different species. (AdipoGen AG-40B-0103, actually commercially available, and produced and distributed by AdipoGen, SA, Liestal, Switzerland).

Palmitic acid has been dissolved in 0.1 mol/l NaOH at 70° C. for 30 min; then 5 mmol/l palmitic acid has been complexed to 10% fatty acid free BSA (palmitic acid:BSA, molar ratio 3.3:1).

Effects of the Conditioned Medium from L6 Myocytes Exposed to Palmitate for Different Periods on the Apoptosis of INS-1E Pancreatic Beta-Cells.

Figure 1:
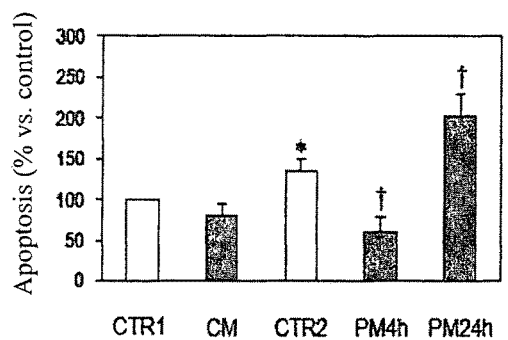
FIG. 1 shows the results of experiments carried out to evaluate the effects of the conditioned medium from myocytes exposed to palmitate for different periods, on the apoptosis of the pancreatic beta-cells.
Figure 1:
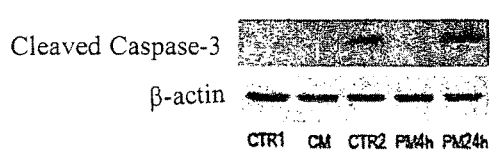
Figure 1:
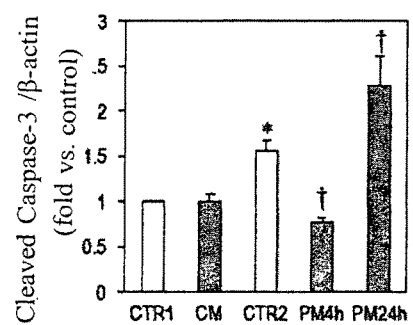

L6 myocytes have been cultured for 4 or 24 h with palmitate (0.5 mM); then, the INS-1E pancreatic beta-cells have been cultured for 24 h in the conditioned medium from myocytes exposed to palmitate (PM4h and PM24h) and with the addition of two control conditions including the INS-1E culture with a non-conditioned medium from myocytes with (CTR2) or without (CTR1) the presence of palmitate for 24 h. Under such conditions the apoptosis of the beta-cells has been measured (by ELISA assay for the detection of cytoplasmic oligonucleosomes, and by detecting the cleavage of caspase-3). Neither the medium without L6 (CTR1), nor the presence of myocytes in the medium (CM) modified the beta-cells apoptosis. The addition of palmitate to the culture medium free of L6 (CTR2) determined an increase of the beta-cells death and of the cleavage of caspase-3 (from 1.3 times to 1.5-times, respectively) (*p<0.05 vs. CTR1; FIG. 1a, b). The measured apoptosis with both methods resulted to be increased by about 1.5 times even in the INS-1E cultured in a conditioned medium from L6 treated with palmitate for 24 h with respect to CTR2 (PM24h) (†p<0.05 vs. CM, CTR1, CTR2). On the contrary, when the medium was from myocytes exposed to fatty acid for 4 h only, the concentration of cytoplasmic oligonucleosomes and the cleavage of caspase-3 of the beta-cells was reduced (†p<0.05 vs. CM, CTR1, CTR2; FIG. 1a, b). The data are reported as average±standard deviation and have been analyzed by means of Student's t test or ANOVA. The statistical significance was set to a value of P<0.05.

Figure 2:
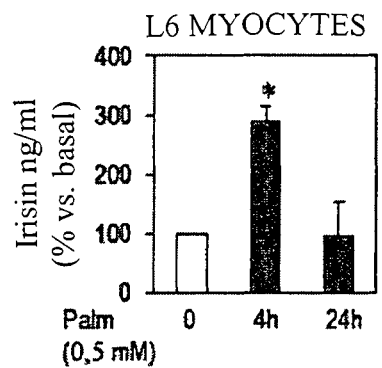
FIG. 2 shows the results of experiments carried out to evaluate the effects of palmitate on the expression and secretion of irisin in rat and human myocytes.
Figure 2:
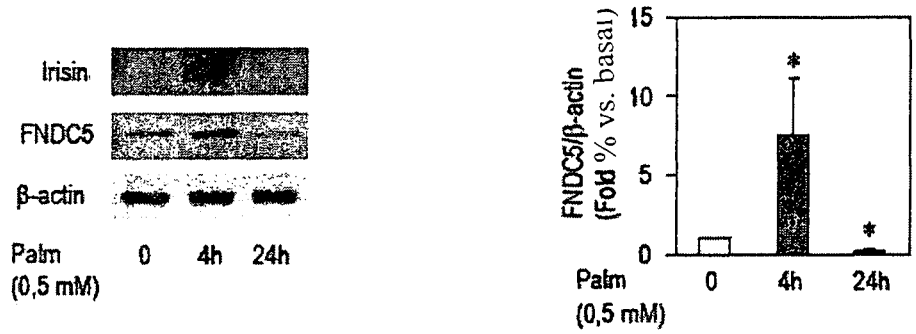
Figure 2:
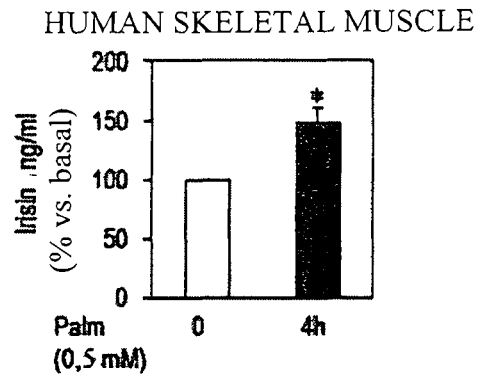

Effects of Palmitate on the Expression and Secretion of Irisin from Rat and Human Myocytes The exposure of both rat and human myocytes to palmitate for 4 h determined an increase of the irisin levels in the culture medium, as measured by ELISA assay, respectively by 2.8 times and by 1.4 times (*p<0.05 vs. basal; FIGS. 2a, c), as is in the cell content of FNDC5 protein and in the fragment corresponding to irisin, cleaved and detected in the culture medium, with respect to myotubes not exposed to the fatty acid (*p<0.05 vs. basal; FIG. 2b). On the contrary, when the myotubes have been treated for 24 h, the levels of FNDC5 protein and irisin in the culture medium were not detectable (*p<0.05 vs. basal; FIG. 2b). The data are reported as average±standard deviation and have been analyzed by means of Student's t test or ANOVA. The statistical significance was set to a value of P<0.05.

Effects of a Hyperlipidic Diet on the Irisin Plasma Levels

Figure 3:
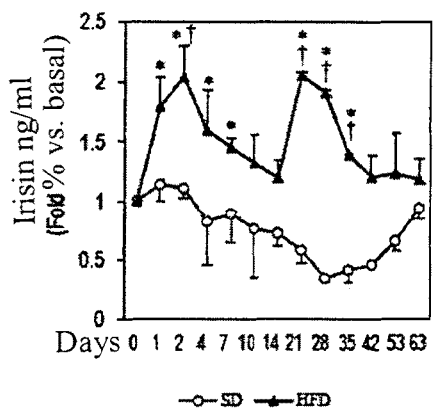
FIG. 3 shows the results of experiments carried out to evaluate the effects of a hyperlipidic diet on the irisin plasma levels.
Figure 3:
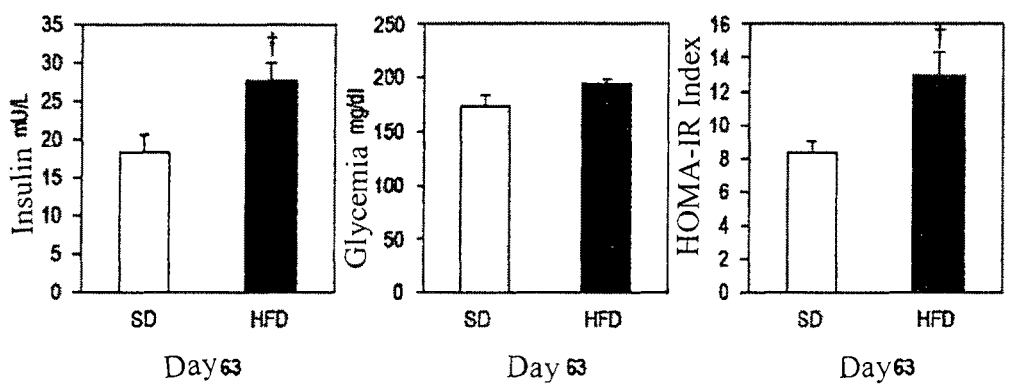

CD-1 male mice (n=15) have been fed from the fifth week of life with a diet rich in saturated fats (provided by Mucedola company) (HFD) and compared with mice fed with a standard diet (n=15) (SD) for 63 days. The measurement of irisin plasma levels showed a statistical significant increase of this protein in the mice fed with an hyperlipidic diet with respect to day 0 (*p<0.05 vs. day 0; FIG. 3a); on the contrary, no irisin increase has been detected in mice fed with a standard diet. Moreover, the irisin levels were significantly higher in mice fed with a hyperlipidic diet with respect to mice fed with a standard diet (†p<0.05 vs. SD; FIG. 3a). The hyperlipidic diet produced a statistical significant increase of the blood insulin levels at day 63 (by 1.5 time, †p<0.05 vs. SD; FIG. 3b) with an increase of the insulin-resistance index (HOMA-IR) (by 1.5 times, †p<0.05 vs. SD; FIG. 3b). These results suggest that the first response to HFD is the increase of the irisin levels, that could contribute to the improvement of the glucose levels, while later the reduction of irisin is associated with the insulin-resistance condition. The data are reported as average ±standard deviation and have been analyzed by means of Student's t test or ANOVA. The statistical significance was set to a value of P<0.05.

Effects of Irisin in Pancreatic Beta-Cells:

Synthesis and Secretion of Glucose-Stimulated Insulin (GSIS).

In order to evaluate the effects of irisin on the production of insulin in pancreatic beta-cells, INS-1E rat insulinoma cells and murine pancreatic islets have been treated with recombinant irisin (100 nM) for different periods (from 30 to 120 minutes). The expression of insulin gene has been evaluated by RT-qPCR by using specific primers for the rat insulin gene:

```
Forward:
                                            (SEQ. ID NO. 1)
    5'-CTGCCCAGGCTTTTGTCAA-3'

Reverse:
                                            (SEQ. ID NO. 2)
    5'-TCGCCACACACCAGGTACAGA-3'
``` and for the mouse:

```
Forward:
                                            (SEQ. ID NO. 3)
    5'-ACCCACCCAGGCTTTTGTC-3'

Reverse:
                                            (SEQ. ID NO. 4)
    5'-TCCCCACACACCAGGTAGAGA-3'
```

The 18S endogenous gene has been used as control, both for the rat:

```
Forward:
                                            (SEQ. ID NO. 5)
    5'-TGATTAAGTCCCTGCCCTTTGT-3';

Reverse:
                                            (SEQ. ID NO. 6)
    5'-GATCCGAGGGCCTCACTAAAC-3'
``` and the mouse:

```
Forward:
                                            (SEQ. ID NO. 7)
    5'-GGCGTCCCCCAACTTCTTA-3';

Reverse:
                                            (SEQ. ID NO. 8)
    5'-AGGGCATCACAGACCTGTTATTG-3'
```

Figure 4:
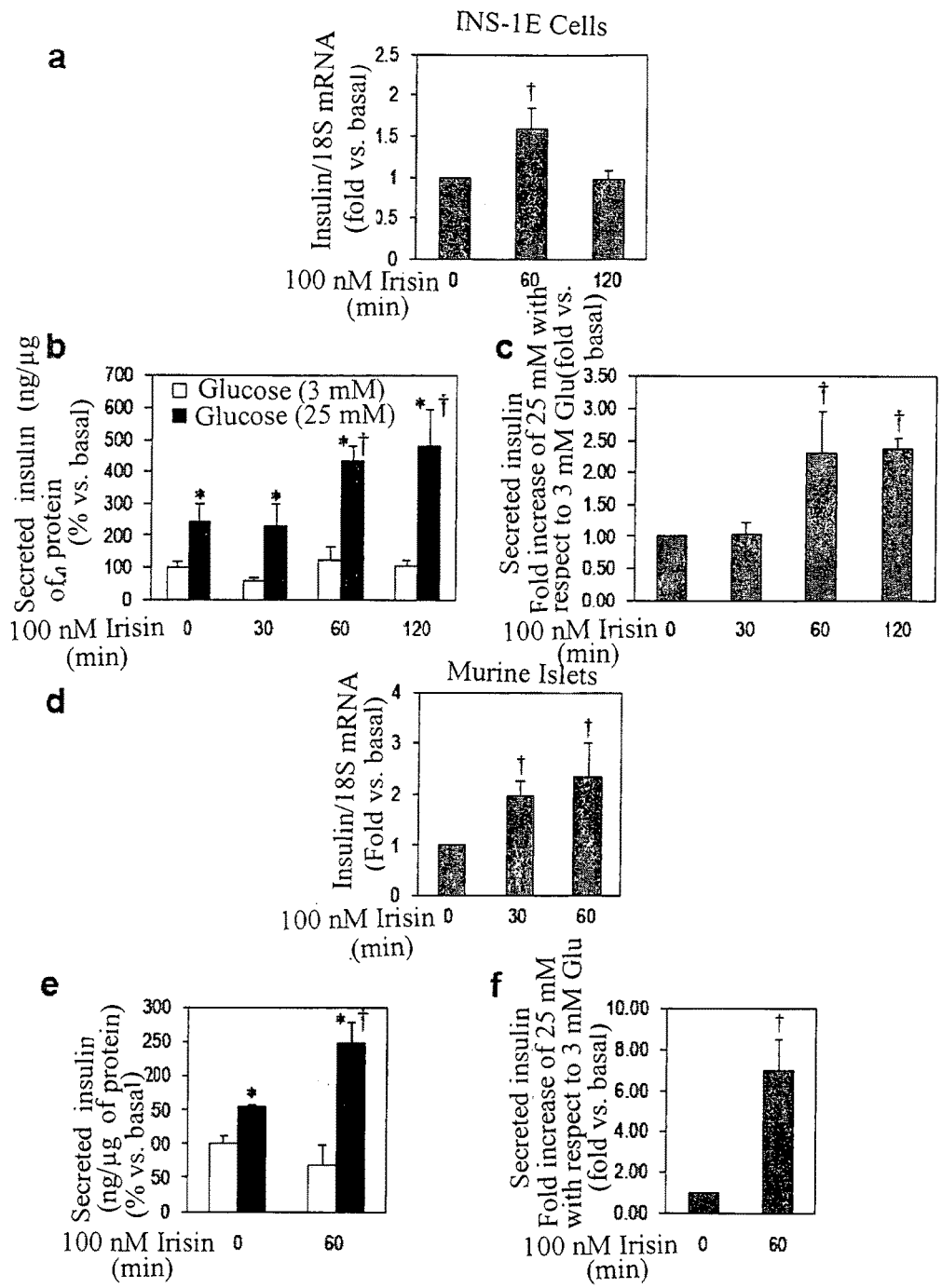
FIG. 4 shows the results of experiments carried out to evaluate the effects of irisin on the synthesis and secretion of glucose-stimulated insulin (GSIS) in pancreatic beta-cells.

The treatment of the INS-1E cells with irisin (100 nM) increased the insulin biosynthesis with respect to the basal state (by 1.6 times after 60 minutes; †p<0.05 vs. basal; FIG. 4a). Similar results have been obtained in the murine pancreatic islets, where irisin increased the insulin biosynthesis by 1.9 times after 30 minutes and by 2.3 times after 60 minutes (†p<0.05 vs. basal; FIG. 4d).

In order to evaluate the effects of irisin on the insulin secretion, INS-1E rat insulinoma cells and murine pancreatic islets have been treated with recombinant irisin (100 nM) for different periods (from 30 to 120 minutes) and then cultured for 1 h with Krebs Ringer Buffer (KRB) containing low (3 mmol/l) or high (25 mmol/l) glucose concentrations. Insulin secretion in the culture medium was evaluated by ELISA assay (Mercodia AB, Sylveniusgatan, Uppsala, Sweden). It has been observed that 25 mmol/l glucose increased the insulin secretion with respect to 3 mmol/l glucose in the INS-1E cells (by 2.5 times; *p<0.05; FIG. 4b) and in the murine pancreatic islets (by 1.5 times; *p<0.05; FIG. 4e). The treatment of the INS-1E cells with irisin (100 nM) enhanced the insulin secretion induced by the high glucose with respect to the basal state (by 1.8 times after 60 minutes and by 1.9 times after 120 minutes †p<0.05 vs. basal; FIG. 4b), as well as the high/low glucose insulin secretion ratio with respect to the state without irisin (by 2.3 times after 60 minutes and by 2.4 times after 120 minutes †p<0.05 vs. basal; FIG. 4c). Similar results have been obtained in the murine pancreatic islets, wherein irisin also increased the insulin release (by 1.6 times †p<0.05 vs. basal; FIG. 4e) and the high/low glucose insulin secretion ratio (by 7 times †p<0.05 vs. basal; FIG. 4f). The data are reported as average±standard deviation and have been analyzed by means of Student's t test or ANOVA. The statistical significance was set to a value of p<0.05.

Beta-Cell Proliferation

Figure 5:
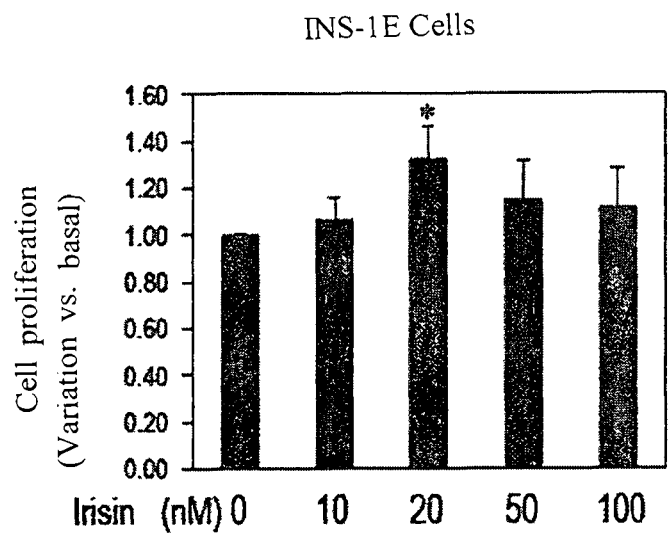
FIG. 5 shows the results of experiments carried out to evaluate the effects of irisin on the proliferation of pancreatic beta-cells.
Figure 5:
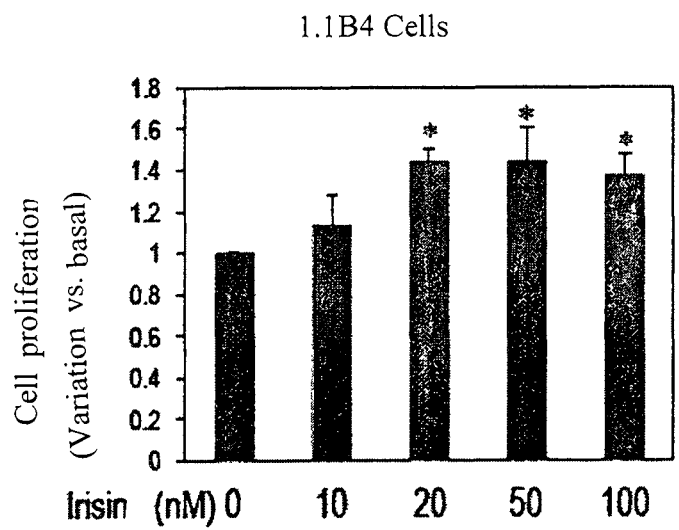

In order to study the irisin effects on the proliferation of pancreatic beta-cells, INS-1E rat insulinoma cells and 1.1B4 human pancreatic beta-cells have been stimulated with recombinant irisin at different concentrations (from 10 to 100 nM) for 24 h. The cell proliferation has been evaluated by means of BrdU incorporation assay (Abcam). Irisin (20 nM) determined an increase by about 1.32 times of the proliferation of INS-1E cells (*p<0.05 vs. basal; FIG. 5a). Moreover, the proliferation of the 1.1B4 beta-cells is increased by irisin at the 20, 50 and 100 nM concentrations respectively by 1.44, 1.43 and 1.36 times (*p<0.05 vs. basal; FIG. 5b).

The data are reported as average ±standard deviation and have been analyzed by means of Student's t test or ANOVA. The statistical significance was set to a value of p<0.05.

Beta-Cells Apoptosis

Figure 6:
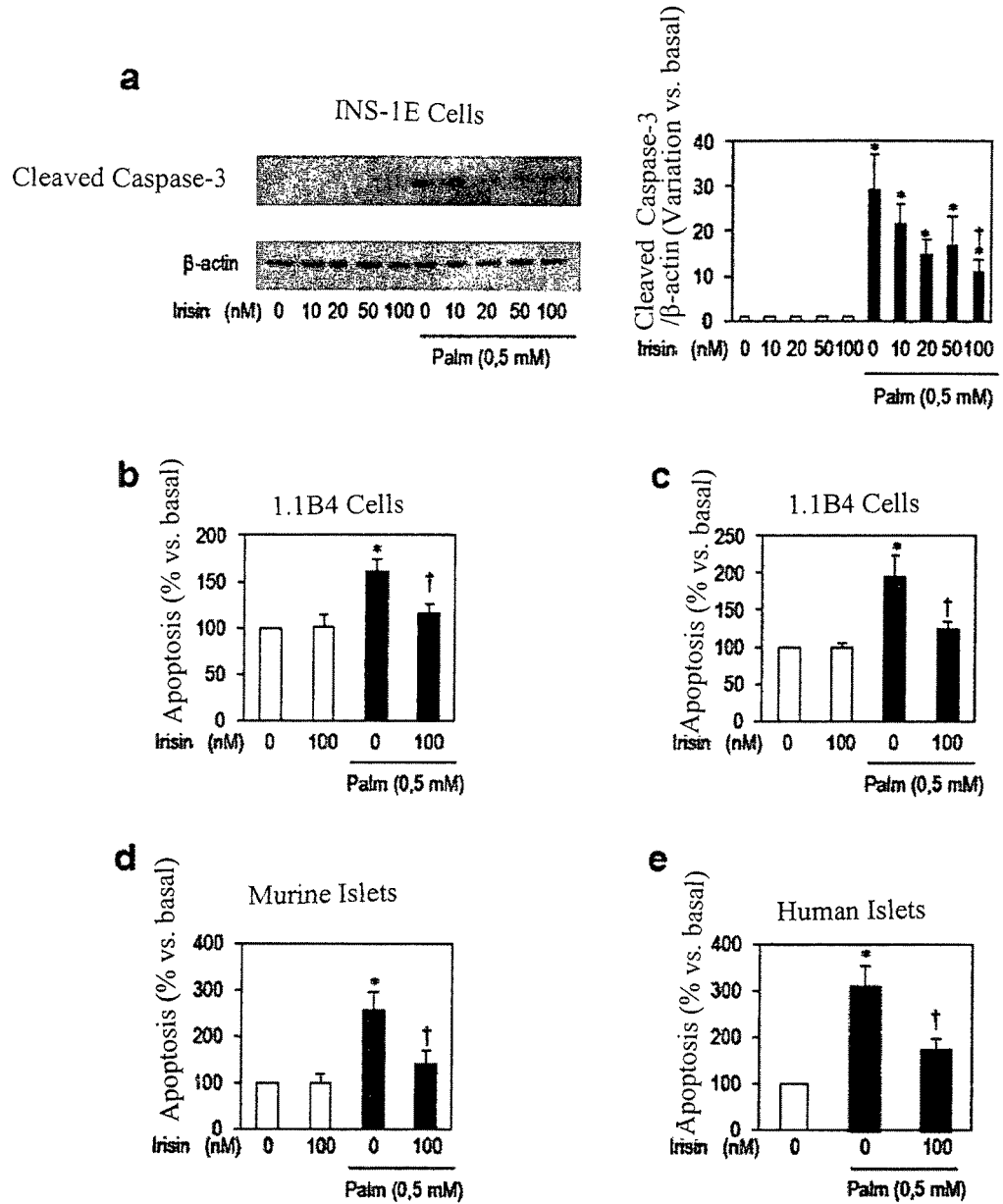
FIG. 6 shows the results of experiments carried out to evaluate the ability of irisin to prevent the beta-cells apoptosis induced by high levels of fatty acids.

In order to study the irisin ability to prevent the beta-cell apoptosis induced by high levels of fatty acids, the INS-1E cells have been stimulated with increasing doses of recombinant irisin (from 20 to 100 nM) for 24 h and later cultured with or without palmitate (0.5 mM) for 24 h. Apoptosis has been evaluated by measuring the cleaved caspase-3 levels by immunoblotting. It has therefore been observed that palmitate increases the levels of cleaved caspase-3 (by about 30 times *p<0.05 vs. no palmitate; FIG. 6a), but the preincubation of beta-cells with irisin reduces the cleavage of caspase-3 starting from a concentration of 20 nM which becomes significant at 100 nM (†p<0.05 vs. palmitate; FIG. 6a). These results observed in INS-1E cells (*p<0.05 vs. no palmitate; †p<0.05 vs. palmitate; FIG. 6b) have been confirmed in 1.1B4 HPC human beta-cells (*p<0.05 vs. no palmitate; †p<0.05 vs. palmitate; FIG. 6c), in murine pancreatic islets (*p<0.05 vs. no palmitate; †p<0.05 vs. palmitate; FIG. 6d) and in human pancreatic islets (*p<0.05 vs. no palmitate; †p<0.05 vs. palmitate; FIG. 6e), by measuring the apoptosis by means of an ELISA assay to detect the cytoplasm oligonucleosomes (Roche Biochemicals Indianapolis Ind., USA). The different cell systems have been incubated with 100 nM irisin for 24 h and then treated with 0.5 mM palmitate for 24 h. The obtained results show that, in all the investigated cell systems, palmitic acid increases the apoptosis levels in a statistical significant way, but the preincubation of the beta-cells with 100 nM irisin reduces the apoptosis levels induced by the fatty acid.

The data are reported as average±standard deviation and have been analyzed by means of Student's t test or ANOVA. The statistical significance was set to a value of p<0.05.

The invention claimed is:

1. A method for the preservation of the functionality and survival of cells of pancreatic islets comprising administering to a subject with pancreas diseases or dysmetabolic conditions in need thereof, an effective amount of Irisin.

2. The method according to claim 1, wherein said cells of the pancreatic islets are beta-cells.

3. The method according to claim 2, wherein said administering an effective amount of Irisin comprises an induction of insulin synthesis that preserves the functionality and survival of cells of pancreatic islets.

4. The method according to claim 2, wherein said administering an effective amount of Irisin comprises a stimulation of insulin secretion that preserves the functionality and survival of cells of pancreatic islets.

5. The method according to claim 1, wherein said administering an effective amount of Irisin comprises promotion of a proliferation of said cells of the pancreatic islets that preserves the functionality and survival of cells of pancreatic islets.

6. The method according to claim 1, wherein said administering an effective amount of Irisin comprises a reduction of death of said cells of the pancreatic islets that preserves the functionality and survival of cells of the pancreatic islets.

7. A method for the preservation of the functionality and survival of cells of pancreatic islets, comprising administering to a subject with pancreas diseases or dysmetabolic conditions in need thereof an effective amount of a composition comprising Irisin.

8. The method according to claim 7, wherein said composition contains at least one of pharmaceutical excipients and pharmaceutical additives.

* * * * *

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: primer forward - rat insulin gene

<400> SEQUENCE: 1
ctgcccaggc ttttgtcaa                                                19

<210> SEQ ID NO 2
<211> LENGTH: 21
<212> TYPE: DNA
<213> ORGANISM: Artificial Sequence
<220> FEATURE:
<223> OTHER INFORMATION: primer reverse - rat insulin gene

<400> SEQUENCE: 2
tcgccacaca ccaggtacag a                                             21

<210> SEQ ID NO 3
<211> LENGTH: 19
<212> TYPE: DNA
<213> ORGANISM: Artificial Sequence
<220> FEATURE:
<223> OTHER INFORMATION: primer forward - mouse insulin gene

<400> SEQUENCE: 3
acccacccag gcttttgtc                                                19

<210> SEQ ID NO 4
<211> LENGTH: 21
<212> TYPE: DNA
<213> ORGANISM: Artificial Sequence
<220> FEATURE:
<223> OTHER INFORMATION: primer reverse - mouse insulin gene
```

```
-continued

<400> SEQUENCE: 4
tccccacaca ccaggtagag a                                              21

<210> SEQ ID NO 5
<211> LENGTH: 22
<212> TYPE: DNA
<213> ORGANISM: Artificial Sequence
<220> FEATURE:
<223> OTHER INFORMATION: primer forward - rat 18S gene

<400> SEQUENCE: 5
tgattaagtc cctgcccttt gt                                             22

<210> SEQ ID NO 6
<211> LENGTH: 21
<212> TYPE: DNA
<213> ORGANISM: Artificial Sequence
<220> FEATURE:
<223> OTHER INFORMATION: primer reverse - rat 18S gene

<400> SEQUENCE: 6
gatccgaggg cctcactaaa c                                              21

<210> SEQ ID NO 7
<211> LENGTH: 19
<212> TYPE: DNA
<213> ORGANISM: Artificial Sequence
<220> FEATURE:
<223> OTHER INFORMATION: primer forward - mouse 18S gene

<400> SEQUENCE: 7
ggcgtccccc aacttctta                                                 19

<210> SEQ ID NO 8
<211> LENGTH: 23
<212> TYPE: DNA
<213> ORGANISM: Artificial Sequence
<220> FEATURE:
<223> OTHER INFORMATION: primer reverse - mouse 18S gene

<400> SEQUENCE: 8
agggcatcac agacctgtta ttg                                            23
```